United States Patent [19]
Plotkin

[11] Patent Number: 5,851,486
[45] Date of Patent: *Dec. 22, 1998

[54] SPRAY SPUN FILTER CARTRIDGES FOR CARDIOTOMY FILTER/DEFOAMER

[75] Inventor: Neil D. Plotkin, Pasadena, Calif.

[73] Assignee: Medtronic, Inc., Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 643,124

[22] Filed: Apr. 30, 1996

[51] Int. Cl.⁶ .............................. A61M 1/14; B01D 27/00
[52] U.S. Cl. ................... 422/44; 422/48; 604/5; 604/6; 210/436; 96/176
[58] Field of Search .............. 422/44, 48; 604/4, 604/5, 6, 406; 210/436, 472, 445, 453, 446; 96/176; 55/528; 95/242, 157

[56] References Cited

U.S. PATENT DOCUMENTS

| | | | |
|---|---|---|---|
| 3,801,400 | 4/1974 | Vogt et al. | 156/167 |
| 3,993,461 | 11/1976 | Leonard et al. | 96/179 |
| 4,664,682 | 5/1987 | Monzen | 96/179 |
| 4,743,371 | 5/1988 | Servas et al. | 210/188 |
| 5,039,430 | 8/1991 | Corey, Jr. | 210/806 |
| 5,340,479 | 8/1994 | Szczepanski et al. | 210/497.1 |

FOREIGN PATENT DOCUMENTS 01022395  1/1989  Japan .

OTHER PUBLICATIONS

English language translation of JP 01022305 (Yashushi), Jan. 25, 1989.
Japio abstract of Jo Yasushi (JP01022305), Jan. 25, 1989.
Caplus abstract of Jo Yasushi (JP01022305), Jan. 25, 1989.
Wpids abstract of Jo Yasushi (JP01022305), Jan. 25, 1989.
Osmonics, Inc. catalog of Hytrex II Cartridge filters, 1987.

Primary Examiner—William H. Beisner
Assistant Examiner—Alex Noguerola
Attorney, Agent, or Firm—Harry G. Weissenberger

[57] ABSTRACT

A simple, self-supporting cardiotomy filter/defoamer is formed by a 20 μm cylindrical spray spun hollow plastic filter cartridge impregnated with an anti-foaming agent.

7 Claims, 2 Drawing Sheets

SPRAY SPUN FILTER CARTRIDGES FOR CARDIOTOMY FILTER/DEFOAMER

FIELD OF THE INVENTION

This invention relates to cardiotomy filter/defoamers used in open heart surgery, and more particularly to a spray spun filter cartridge which reduces manufacturing cost and improves patient safety.

BACKGROUND OF THE INVENTION

During open-heart surgery in which the patient's heart is stopped, blood circulation is maintained by a heart-lung machine which diverts the patient's blood from the vena cava, oxygenates it, and pumps it back into the patient's aorta. For the most part, the patient's circulatory system and the heart-lung machine constitute a closed circuit in which no air is present.

In the course of the surgery, however, a substantial amount of blood leaks into the surgical field. This blood must be recovered and returned to the cardiopulmonary blood circuit of the heart-lung machine to avoid excessive blood loss.

The surgical field is suctioned on command of the surgeon primarily to remove blood or other fluids to allow clear visualization and a dry field in which to perform the surgical tasks. The process of suctioning generally mixes large volumes of air into the scavenged blood which, due to the properties of blood proteins, subsequently forms a stable foam in the cardiotomy reservoir into which the scavenged blood is discharged. This foam is undesirable because air contact is generally traumatic to the blood elements, and the foam often will expand to greater than the volume of the container and then flow out onto the floor. The foam must be completely broken so that air bubbles, which would cause harm to the patient if they entered the circulatory system, are eliminated.

The filter/defoamer section of the cardiotomy reservoir is desired to both filter and defoam the blood suctioned from the surgical field prior to return to the patient's circulatory system. Failure to adequately remove debris or to eliminate air bubbles from the blood could result in significant harm to the patient. Thus, filtration is required to remove any bits of tissue, bone, fat, or other debris that may be present in the chest cavity blood which is sucked up by the cardiotomy suction system and deposited into the cardiotomy reservoir for transference back into the circulatory system. Typically a filter having at least 90% efficiency at 20 microns is utilized for this task.

Conventionally, a filter/defoamer cartridge for this purpose consists of a plastic support structure which supports, in the flow direction, successive layers of a coarse open-celled plastic foam coated with an anti-foaming chemical; a filter felt; a fine open-celled plastic foam coated with anti-foaming chemicals; and a tricot knit fabric.

The multiplicity of materials used in conventional filter/defoamers introduces many non-biological surfaces which tend to increase the human immune system's foreign body response. In addition, one drawback of the small pores of the fine open-cell foam is that foam can be generated in the blood downstream of the filter if a large volume of air is entrained along with the liquid stream. Also, the complex construction of the disposable conventional filter/defoamers adds substantially to their cost.

SUMMARY OF THE INVENTION

The invention overcomes the above-described disadvantages of the prior art by substituting for the conventional multi-layer filter/defoamer construction a single, self-supporting filter/defoamer element of spray spun plastic (typically polypropylene) impregnated with anti-foaming chemicals.

DESCRIPTION OF THE PREFERRED EMBODIMENT

Figure 1:
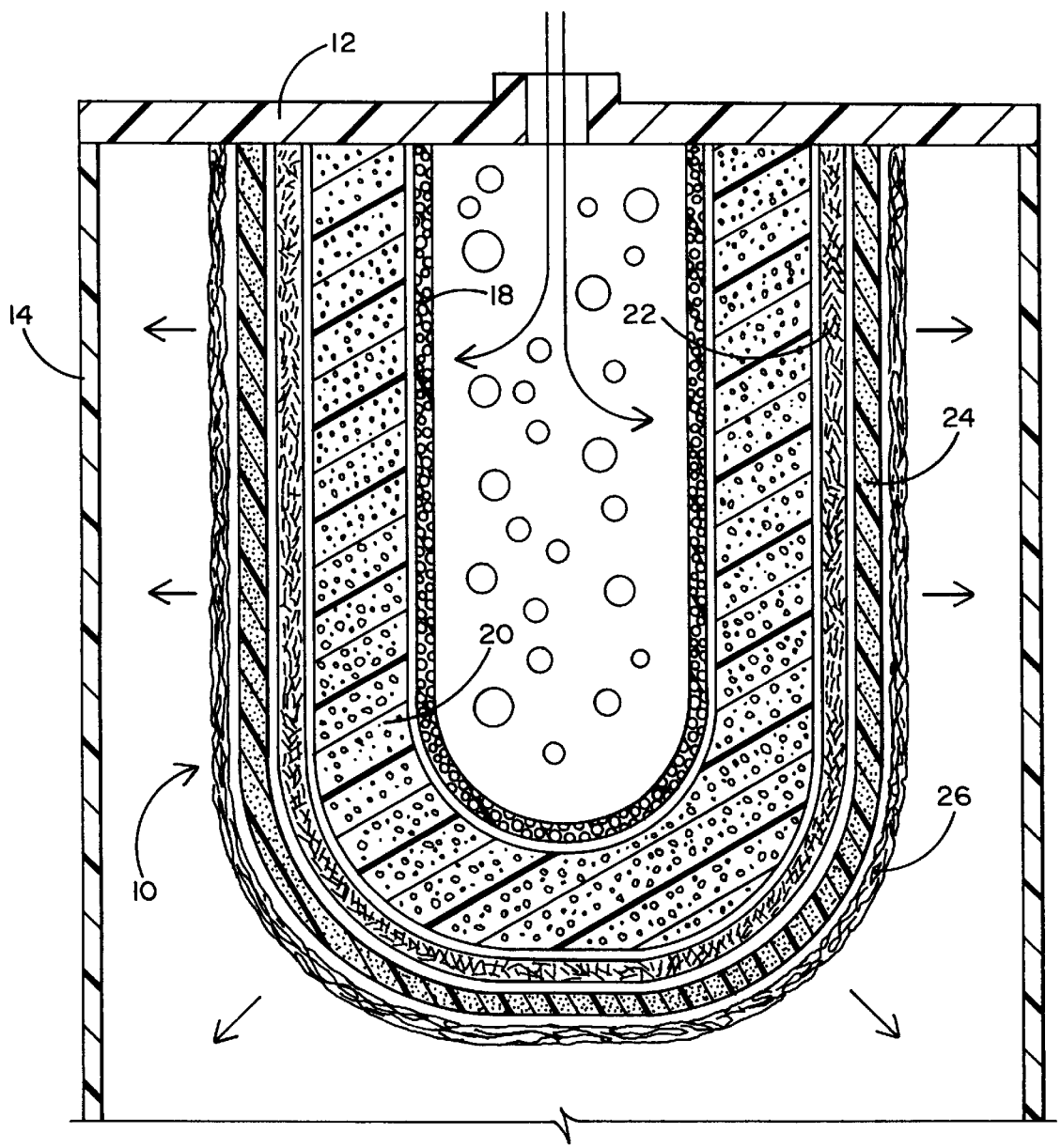
FIG. 1 is a vertical section of a conventional filter/defoamer.

FIG. 1 shows the conventional construction of a blood filter/defoamer assembly. The assembly 10 is typically attached to the lid 12 of a cardiotomy reservoir 14. Scavenged blood is introduced into the center of the filter/defoamer cartridge 16 and flows thorough the filtering and defoaming layers of the cartridge 16 into the reservoir 14.

At the core of the cartridge 16 is a plastic support structure 18. This support structure is required because the active layers of the cartridge 16 are not self-supporting.

Immediately outward of the support structure 18 is a layer 20 of coarse open celled plastic foam. The foam 20 is coated with a conventional anti-foam chemical. The foam layer 20 is intended to act as a crude prefilter and also to provide a large amount of surface area to cause intimate contact of the blood foam with the thin coating of anti-foaming chemicals. In addition it aids in mechanically breaking the blood foam.

The foam layer 20 is surrounded by a filtering felt layer 22 which is typically a thermally or adhesively bonded nonwoven mesh, calendered on one or both sides. It is intended to capture particulate matter, blood clots, etc. that may be present in the returning blood flow. The calendering, which is present primarily on the downstream side, is intended to reduce the shedding of the constituent fibers of the non-woven mat.

Following the felt layer 22 in the flow direction is a fine open cell plastic foam layer 24. This foam layer is also coated with antifoaming chemicals. The smaller pore size increases the contact of the blood with the surface and helps to break down small bubbles.

Finally, a tricot knit fabric sock 26 covers the outside of the foam layer 24. The tricot knit sock acts as an additional bubble removing surface and provides a cosmetically acceptable outer surface for the cartridge 16.

Figure 2:
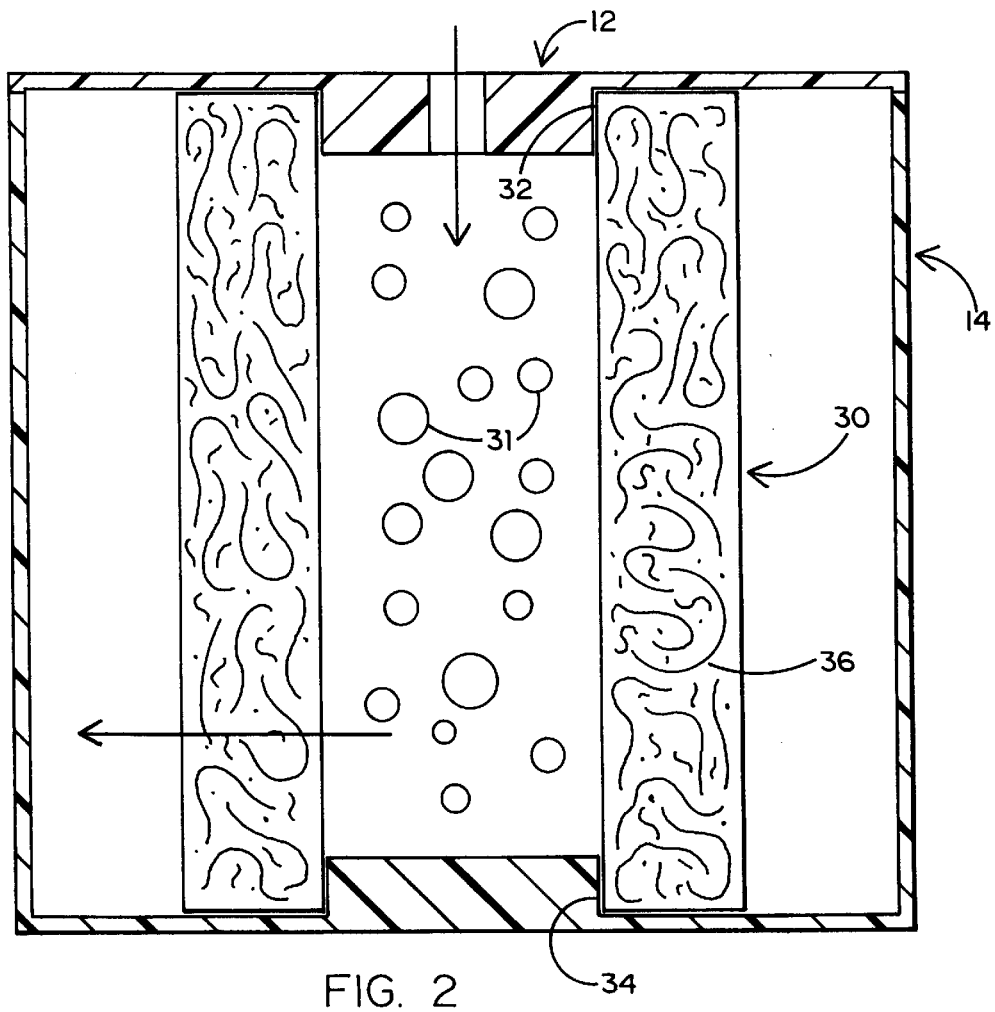
FIG. 2 is a vertical section of a filter/defoamer in accordance with the invention.

FIG. 2 schematically shows a similar cardiotomy reservoir 14 using the inventive cartridge 30 instead of the cartridge 16. The cartridge 30 is a self-supporting spray spun filter cartridge impregnated with a suitable conventional anti-foaming agent which breaks down the foam 31, and thus needs merely to be held between flanges 32, 34 of the lid 12 and reservoir 14, respectively.

Spray spun filter cartridges are commercially available products, e.g. cartridges manufactured by Hytrex II, Osmonics, Inc. typically used for high purity industrial filtration applications. The filters are formed by spraying molten plastic (typically polypropylene) with a high velocity air stream across a gap onto a rotating mandrel to form a continuous cylindrical log which is then cut to length. The molten plastic stream is fibrillated by the air and deposits a complex filter matrix of thermally bonded microfibers. The outside of the cylinder can be calendered to improve the appearance and to further prevent material shedding.

Figure 3:
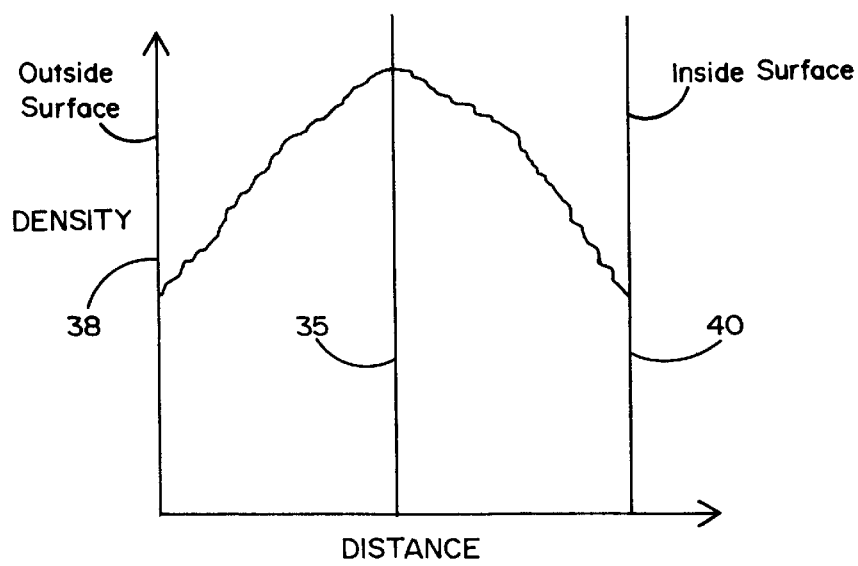
FIG. 3 is a graph showing the variation of the density of the cartridge material between the inner and outer surfaces of the cartridge.

The key property of spray spun filter cartridges which makes them suitable for use as a cardiotomy filter/defoamer is the graded density of the cartridge which is illustrated in FIG. 3. The highest density (smallest particle size retention) is towards the center 35 of the annular cylindrical ring 36 of the cartridge 30, and the lowest density is towards the outer and inner surfaces 38, 40, respectively, of the annular cylindrical ring 36. This essentially duplicates the foam-felt-foam structure of the conventional filter/defoamer of FIG. 1. Commercially available spray-spun cartridges can provide at least the 90% filtration efficiency at 20 µm required for cardiotomy use.

Another advantage of the spray-spun cartridge material is that the spray-spun cartridges useful for cardiotomy are made completely from polypropylene with very low levels of extractables or other chemical contaminants. Polypropylene is a common component in blood oxygenators and other components in the heart bypass circuit. For these uses, polypropylene can be rendered even more bio-compatible, if necessary, through the use of suitable conventional surface modification technologies.

It will be seen that the invention provides a simple, inexpensive, effective, and highly biocompatible blood filter/defoamer particularly useful for cardiotomy.

It is understood that the exemplary cardiotomy filter/defoamer described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

I claim:

1. A cardiotomy filter/defoamer, comprising:
   a) a reservoir;
   b) a filter/defoamer; and
   c) a blood inlet for receiving blood to be placed in said reservoir, said blood inlet being so positioned that blood entering said reservoir must flow through said filter/defoamer prior to being placed in said reservoir;
   d) said filter/defoamer consisting of a self-supporting hollow cylinder formed from a complex matrix of spray spun non-hollow plastic fibers impregnated with an anti-foaming agent, said matrix having an effective pore size such as to pass blood cells but retain cardiotomy debris, and also a graded density between the outer and inner surfaces of the hollow cylinder.

2. The filter/defoamer of claim 1, in which said matrix has a filtration capability of substantially 20 µm.

3. The filter/defoamer of claim 1, in which the material of said plastic fibers is polypropylene.

4. The filter/defoamer of claim 1, in which said hollow cylinder is in said reservoir.

5. The filter/defoamer of claim 1, in which said reservoir has a body and a lid, and said hollow cylinder is self-supported between said body and said lid.

6. The filter/defoamer of claim 1, in which the outer surface of said hollow cylinder is calendered.

7. A cardiotomy filter/defoamer, comprising:
   a) a reservoir:
   b) a filter/defoamer cartridge; and
   c) a blood inlet for receiving blood to be placed in said reservoir, said blood inlet being so positioned that said blood must flow through said filter/defoamer prior to being placed in said reservoir;
   d) said filter/defoamer cartridge comprising a self-supporting hollow cylindrical filter of spray spun plastic forming a complex filter matrix of thermally bonded non-hollow microfibers, said filter matrix being impregnated with an anti-foaming agent; and
   e) the density of said matrix being maximal at substantially the center of said matrix in the direction of blood flow, and minimal at substantially the external surfaces of said matrix, said matrix having an effective pore size such as to pass blood cells but retain cardiotomy debris.

* * * * *